United States Patent [19]

Goth

[11] Patent Number: 4,867,145
[45] Date of Patent: Sep. 19, 1989

[54] ABDOMINAL AND PELVIC AREA SUPPORT

[76] Inventor: Shirley L. Goth, Rte. 3, Box 232, Lenoir City, Tenn. 37771

[21] Appl. No.: 175,299

[22] Filed: Mar. 30, 1988

[51] Int. Cl.$^4$ ............................ A61F 5/24; A61F 5/28
[52] U.S. Cl. .................................. 128/96.1; 128/99.1; 128/105.1
[58] Field of Search ................... 128/96.1, 99.1, 100.1, 128/101.1, 102.1, 105.1, 106.1; 604/390, 391, 392, 401, 402, 403

[56] References Cited

U.S. PATENT DOCUMENTS

| 889,620 | 6/1908 | Klein | 604/402 |
|---|---|---|---|
| 2,523,079 | 9/1950 | Walter et al. | 604/401 |
| 2,577,398 | 12/1951 | Blake | 604/401 |
| 2,691,983 | 10/1954 | Bernard | 604/401 |
| 3,351,062 | 11/1967 | Ferguson | 604/392 |
| 3,417,751 | 12/1968 | Murdoch | 604/401 |
| 3,577,986 | 5/1971 | Regent | 128/96.1 |
| 3,729,004 | 4/1973 | Burger | 604/401 |
| 4,037,602 | 7/1977 | Hawthorne | 604/390 |
| 4,617,022 | 10/1986 | Pigneul et al. | 604/391 |

Primary Examiner—Robert A. Hafer
Assistant Examiner—Michael Brown
Attorney, Agent, or Firm—Pitts and Brittian

[57] ABSTRACT

An abdominal and pelvic area support (10) for being worn by, and supported by the shoulders of, a wearer (18). The pelvic area support (10) has a support member (12) including a backing panel (36) having first and second opposite end portions (42 and 43) and a narrowed crotch portion (44) therebetween. The support member further includes first and second elongated support panels (38 and 40) secured to the backing panel (36), and disposed such that the first support panel (38) extends from a point at, or proximate, a first corner portion (45) of the first end portion (42) of the backing panel to a point at, or proximate, a further corner (48) of the second end portion (43) of the backing panel (36), and the second support panel (40) extends from a point at, or proximate, a further corner (46) of the first end portion (42) to a point at, or proximate, a first corner portion (47) of the second end portion (43) of the backing panel (36), with the first and second support panels (38 and 40) crossing at a point proximate the crotch portion (44) of the backing panel (36). The pelvic area support (10) also has a harness (16) for engaging and supporting the support member (12) on the shoulders of the wearer (18), and, in the preferred embodiment, a cover garment (14) for covering the support member (12).

13 Claims, 3 Drawing Sheets

ABDOMINAL AND PELVIC AREA SUPPORT

TECHNICAL FIELD

This invention relates to an abdominal and pelvic area support for providing a lifting support to the lower abdomen and pelvic area of a wearer. In this particular invention, the pelvic area support includes a support member provided with a pair of crossing support panels and a harness for supporting the support member.

BACKBROUND ART

When a person is overweight, great stress can be placed on the lower back and other pelvic structures causing pain and damage to such structures due to excess weight being carried in the pelvic area. Further, those who experience problems with incontinence often require pelvic area support in order to support, and relieve pressure on, the bladder. Various pelvic supports are available such as girdles and trusses; however, such conventional supports generally provide support through the exertion of inward force on the pelvic area. Whereas, this inward force stabilizes pelvic structures, the excess weight still must be carried by the lower back and pelvis, and pressure on the bladder is increased rather than relieved. Examples of certain prior art support and garments are disclosed in U.S. Patent Nos. 2,523,079; 2,581,904; 2,638,899; 2,662,526; 2,691,983; 3,025,856; 3,729,004; and 4,617,022.

Therefore, it is an object of the present invention to provide an abdominal and pelvic area support for supporting the lower abdomen and pelvic area.

A further object of the present invention is to provide a pelvic area support which provides a lifting support to the pelvic area and shifts a portion of the burden of carrying the weight of the abdomen and pelvic area to the shoulders of the wearer thereby relieving stress on the lower back and pelvic structures.

Another object of the present invention is to provide a pelvic area support which supports the bladder of the wearer without exerting undue pressure on the bladder.

Yet another object of the present invention is to provide a pelvic area support which is comfortable to wear and inexpensive to manufacture.

DISCLOSURE OF THE INVENTION

Other objects and advantages will be accomplished by the present invention which provides an abdominal and pelvic area support for being worn by and supported by the shoulders of, a wearer. The pelvic area support comprises a support member including a backing panel having first and second opposite end portions with a narrowed crotch portion disposed therebetween, the first end portion having a first and further corner portion and the second end portion having a first and further corner portion. The support member further includes first and second elongated support panels secured to the backing panel and disposed such that the first support panel extends from a point at, or proximate, the first corner portion of the first end portion to a point at, or proximate, the further corner portion of the second end portion, and the second support panel extends from a point at, or proximate, the further corner portion of the first end portion of the backing panel to a point at, or proximate, the first corner portion of the second end portion of the backing panel, with the first and second support panels crossing at a point proximate the crotch portion of the backing panel. The pelvic area support also comprises a harness for engaging and supporting the support member on the shoulders of the wearer. Moreover, in the preferred embodiment, a cover garment is provided for covering the support member and giving the pelvic area support the appearance of a conventional undergarment.

BRIEF DESCRIPTION OF THE DRAWINGS

The above-mentioned features of the invention will become more clearly understood from the following detailed description of the invention read together with the drawings in which.

BEST MODE FOR CARRYING OUT THE INVENTION

Figure 1:
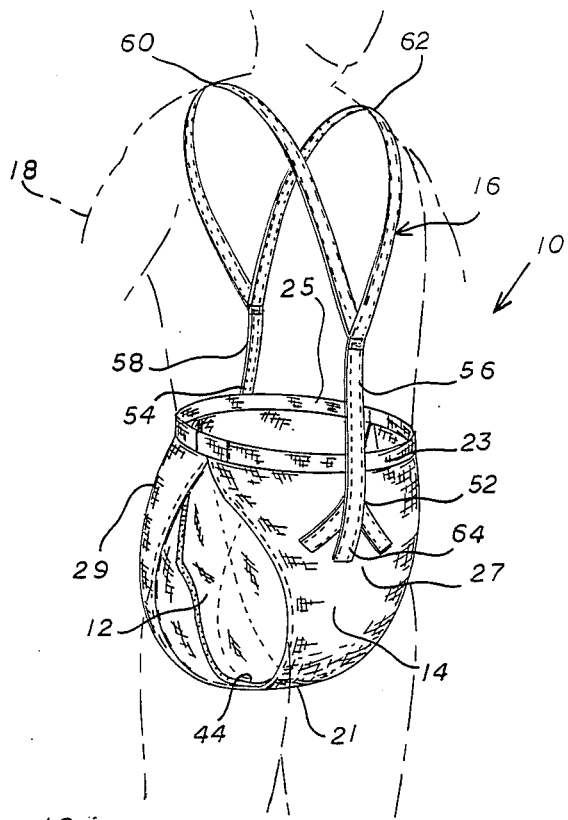
FIG. 1 illustrates a perspective view of an abdominal and pelvic area support of the present invention.

An abdominal and pelvic area support incorporating various features of the present invention is illustrated at 10 in the figures. The support 10 generally comprises a support member 12 covered by an outer cover garment 14, and is provided with a support harness 16 for supporting the support 10 on the body of the wearer 18. As will be discussed in detail below, the abdominal and pelvic area support 10 serves to provide lifting support to the lower abdomen and pelvic area of the wearer with this lifting support being provided primarily by the support member 12 and the harness 16. Accordingly, whereas the cover garment 14 is useful for certain applications, as will be discussed, the garment 14 is optional and the support 10 can comprise only the support member 12 and the support harness 16. (See FIG. 5)

Figure 2:
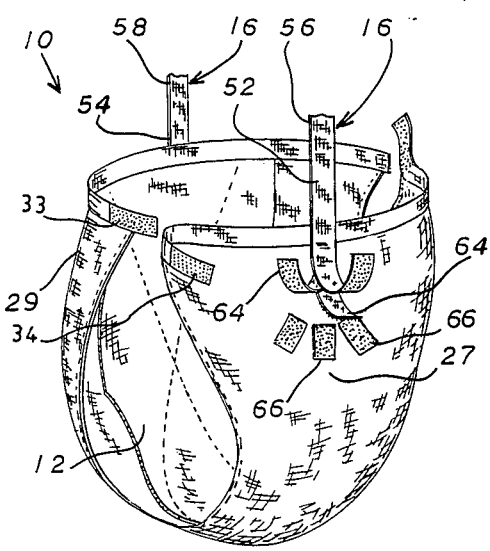
FIG. 2 is a parital perspective view of a pelvic area support of the present invention.

The cover garment 14 generally comprises an hour-glass-shaped body 20 made from a suitable fabric, as, for example, cotton. The body 20 defines a first edge portion 22 and a second edge portion 24, with a narrowed crotch portion 21 defined substantially equidistant therebetween. Secured along the first edge portion 22 is a first waistband portion 23 having first and second end portions 26 and 28, respectively, and secured along the second edge portion 24 is a second waistband portion 25, having first and second end portions 30 and 32, respectively. As illustrated in FIGS. 1 and 2, when worn, the body 20 of the cover garment 14 defines a panty-type garment having front and rear portions 27 and 29, respectively, for covering the pelvic area, with the crotch portion 21 being received between the legs of the wearer 18. Further, the waistband portions 23 and 25 cooperatively provide a supporting waistband about the waist of the wearer 18 for holding the garment 14 in place.

More specifically, securing means are provided for releasably securing the first end portion 26 of the waistband portion 23 to the first end portion 30 of the waistband portion 25, and for releasably securing the second end portion 28 of the waistband portion 23 to the second end portion 32 of the waistband portion 25, to produce a body encircling waistband. As illustrated in the preferred embodiment, such securing means comprises Velcro fasteners, the mating components of which are illustrated at 33 and 34 in the figures. It will be understood that the use of Velcro fasteners allows the size of the waistband to be adjusted, and allows the cover garment 14 to be quickly and easily secured on, or removed from, the body of the wearer. However, it will be understood that other suitable fastening means can be utilized such as snaps, buttons, etc., or the waistband portions 23 and 25 can be integrally formed, or fixedly secured together, if desired. Further, in the preferred embodiment, the waistband portions 23 and 25 are fabricated from an elastic material to effect a secure fit about the waist of the wearer, but it will be understood that various non-elastic materials can be used.

Figure 3:
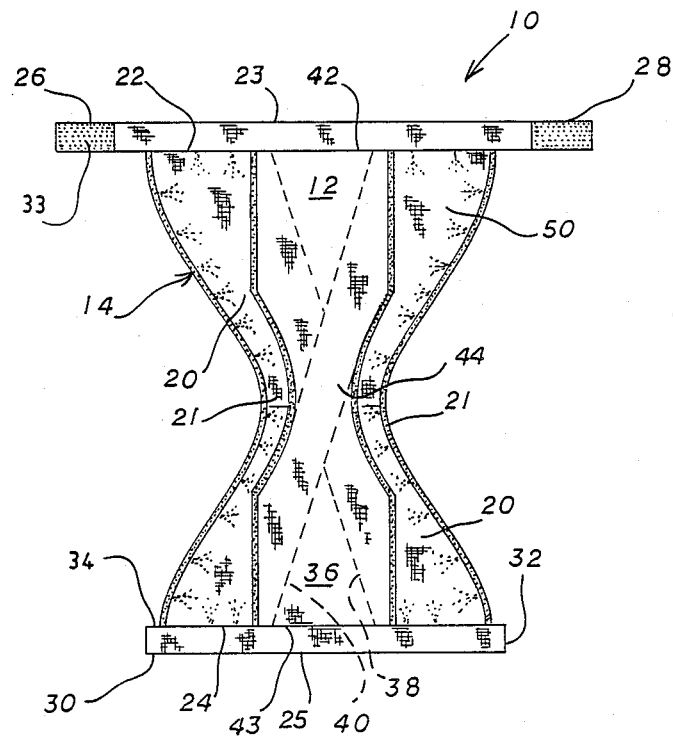
FIG. 3 is a plan view of the interior of the support member and cover garment of a pelvic area support of the present invention.
Figure 4:
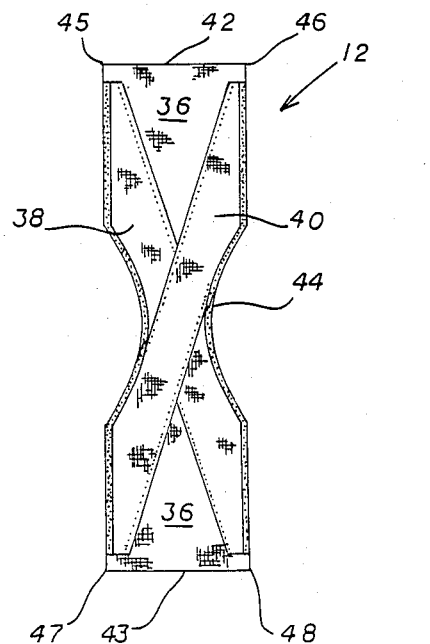
FIG. 4 is a plan view of the support member of a pelvic area support of the present invention.

As is best illustrated in FIGS. 3 and 4, the support member 12 comprises a backing panel 36 to which is secured a pair of crossing elongated support panels 38 and 40, and which is secured to the interior of the cover garment 14, as by sewing. More specifically, the backing panel 36 is generally hourglass-shaped so as to define first and second opposite end portions 42 and 43, respectively, and a narrowed crotch portion 44 disposed substantially equidistant therebetween. The backing panel can be made from various fabrics, as, for example, a cotton fabric. The support panels 38 and 40 overlay and are secured to the backing panel 36 such that the support panel 38 extends from a point at, or proximate, the first corner 45 of the first end portion 42 of the backing panel 36 to a point at, or proximate, the further corner 48 of the second end portion 43 of the backing panel 36, and the support panel 40 extends from a point at, or proximate, the further corner 46 of the first end portion 42 of the backing panel 36 to a point at, or proximate, the first corner 47 of the second end portion 43 of the backing panel 36. Thus, the support panels 38 and 40 cross one another proximate the crotch portion 44, with the panel 40 overlaying the panel 38. Resultantly, the panels 38 and 40 define an X-shaped configuration which extends upwardly from the crotch portion in both front and back which supports and carries the lower abdomen and pelvic area.

It will be understood that in the preferred embodiment, the support panels 38 and 40 are secured to the backing panel 36 by sewing, but other suitable securing means can be used if desired. Further, the panels 38 and 40 are preferably fabricated of a thick durable cloth or webbing material since such panels are the primary support structures of the pelvic area support 10.

Referring once again to FIG. 3, the support member 12 is secured to the cover garment 14 so as to overlay the interior surface 50 of the body 20, and such that the member 12 extends from a point at, or proximate, the first edge portion 22 of the body 20 to a point at, or proximate, the second edge portion 24 of the body 20. In this regard, in the preferred embodiment, the first end portion 42 of the member 12 is secured, as by sewing, to the body 20 at the first edge portion 22 and the second end portion 43 of the member 12 is secured, as by sewing, to the body 20 at the second edge portion 24. Resultantly, when the pelvic area support 10 is worn, the support member 12 is positioned between the cover garment 14 and the body of the wearer, and defines front and rear portions coinciding with the front and rear portions 27 and 29 of the cover garment 14. Thus, the cover garment 14 serves to cover the support member 12 and gives the support 10 the appearance of a conventional undergarment rather than a pelvic area support apparatus.

As illustrated in FIG. 1, the harness 16 is designed to be received over the shoulders of the wearer 18 and secured by its first end portion 52 to the front portion 27 of the cover garment 14, and the support member 12 underlying the garment 14, and by its second end portion 54 to the rear portion 29 of the cover garment 14 and the underlying support member 12. In the preferred embodiment, the harness 16 comprises front and rear straps 56 and 58, respectively, joined by a pair of shoulder straps 60 and 62 which are received over the shoulders of the wearer 18 as illustrated in FIG. 1. However, it will be understood that other harness configurations can be utilized to support the pelvic area support 10 on the shoulders of the wearer. Further, in the preferred embodiment, the first and second end portions 52 and 54 of the harness 16 releasably engage the front and rear portions 27 and 29, respectively, to facilitate putting on and taking off the support 10. Whereas, various means can be utilized to releasably secure the harness 16, in the preferred embodiment, the first and second end portions 52 and 54 of the harness 16 carry three radiating tabs 64, each of which is releasably secured to the cover garment 14 with Velcro fastener. It will be noted that the Velcro coupling members 66 are preferably secured both to the garment 14 and the support member 12 underlying the garment 14 such that the harness 16 directly supports the support member 12.

In the preferred embodiment, the harness 16, or at least a portion thereof, is fabricated of an elastic material such that the harness 16 adjusts to different body sizes and such that the harness 16 exerts a lifting force on the support member 12. This supporting lift provided by the harness 16, coupled with the advantageous crossing configuration of the support panels 38 and 40, serve to lift and support the lower abdomen and pelvic area of the wearer. Resultantly, a substantial portion of the burden of carrying the weight of the abdomen and pelvic area is shifted to the shoulders of the wearer, thereby relieving stress on the lower back and other pelvic structures. Further, the lifting support provided by the pelvic area support 10 supports and relieves pressure on the bladder of the wearer making the support 10 ideal for incontinent wearers. Moreover, the support 10 can be worn over a diaper, or similar garment, thereby holding the diaper in place, with the cover garment 14 serving to give the appearance of a conventional undergarment.

Figure 5:
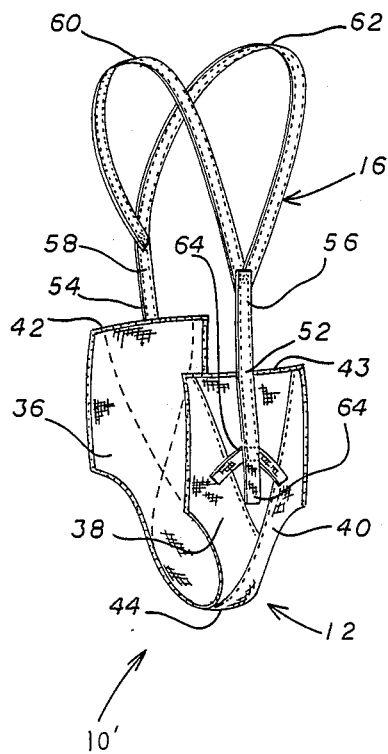
FIG. 5 is a perspective view of an alternate embodiment of a pelvic area support of the present invention.

As described above, the cover garment 14 can be omitted if desired. In this regard, FIG. 5 illustrates an alternate embodiment of the support, referenced at 10', comprising only the support member 12 and the harness 16. It will be understood, however, that this alternate embodiment is constructed and functions as described with respect to the support 10 discussed above.

While a preferred embodiment has been shown and described, it will be understood that there is no intent to limit the invention to such disclosure, but rather, it is intended to cover all modifications and alternate constructions falling within the spirit and scope of the invention as defined in the appended claims.

I claim:

1. An abdominal and pelvic area support for being worn by and supported on the shoulders of a wearer, said pelvic area support comprising:

a support member including a backing panel defining first and second oppositely disposed surfaces and first and second opposite end portions, with a narrowed crotch portion disposed therebetween, said first end portion defining first and further corner portions and said second end portion defining first and further corner portions, said support member further including first and second elongated support panels secured to said first surface of said backing panel, said first support panel being disposed so as to extend from a point proximate said first corner portion of said first end portion of said backing member to a point proximate said further corner portion of said second end portion of said backing panel, and said second support panel being disposed so as to extend from a point proximate said further corner portion of said first end portion of said backing panel to a point proximate said first corner portion of said second end portion of said backing panel, whereby said first and second support panels cross at a point proximate said crotch portion of said backing panel to form an X-shaped pattern, said support member defining front and rear portions oppositely disposed with respect to said crotch portion of said backing panel;

a cover garment for being received over and secured to said support member so as to give said pelvic area support the appearance of an conventional undergarment, said cover garment including an hourglass-shaped body defining a first edge portion and a second edge portion and a narrowed crotch portion therebetween, said cover garment further including a first waistband portion secured to said first edge portion of said body and a second waistband portion secured to said second edge portion of said body, each said waistband portion defining first and second end portions, said first end portion of said first waistband portion being releasably secured to said first end portion of second waistband portion, and said second end portion of said first waistband portion being releasably secured to said second end portion of said second waistband portion, said cover garment defining front and rear portions oppositely disposed with respect to said crotch portion of said body; and a harness for engaging and supporting said support member and cover garment on said shoulders of said wearer to thereby cause said support member to contact and support said pelvic area of said wearer, said harness defining a first end portion releasably secured to said front portion of said cover garment, and indirectly secured to said front portion of said support member through said cover garment, and a second end portion releasably secured to said rear portion of said cover garment, and indirectly secured to said rear portion of said support member through said cover garment.

2. The pelvic area support of claim 1 wherein said harness includes a front strap defining said first end portion of said harness and a rear strap defining said second end portion of said harness, and further including a pair of shoulder straps, each having a first end secured to said front strap and a second end secured to said rear strap.

3. The pelvic area support of claim 2 wherein said first and second end portions of said harness each carry a plurality of radiating tabs and wherein said pelvic area support is provided with means for releasably securing said tabs to said support member.

4. The pelvic area support of claim 3 wherein said means for releasably securing said tabs comprises a plurality of hook and loop fasteners.

5. An abdominal and pelvic area support for being worn by and supported on the shoulders of a wearer, said pelvic area support comprising:

a support member including a backing panel defining first and second oppositely disposed surfaces and first and second opposite end portions, with a narrowed crotch portion disposed therebetween, said first end portion defining first and further corner portions and said second end portion defining first and further corner portions, said support member further including first and second elongated support panels secured to said first surface of said backing panel, said first support panel being disposed so as to extend from a point proximate said first corner portion of said first end portion of said backing member to a point proximate said further corner portion of said second end portion of said backing panel, and said second support panel being disposed so as to extend from a point proximate said further corner portion of said first end portion of said backing panel to a point proximate said first corner portion of said second end portion of said backing panel, whereby said first and second support panels cross at a point proximate said crotch portion of said backing panel to form an X-shaped pattern; and a harness for engaging and supporting said support member on said shoulders of said wearer thereby causing said support member to contact and support said abdominal and pelvic area of said wearer.

6. The pelvic area support of claim 5 wherein said support further comprises a cover garment for being received over, attached to and covering said support member so as to give said pelvic area support the appearance of a conventional undergarment.

7. The pelvic area support of claim 6 wherein said cover garment includes an hourglass-shaped body defining a first edge portion and a second edge portion and a narrowed crotch portion therebetween, said cover garment further including a waistband secured to said first and second edge portions for being received around the waist of said wearer so as to support said cover garment.

8. The pelvic area support of claim 7 wherein said waistband comprises a first waistband portion secured to said first edge portion of said body and a second waistband portion secured to said second edge portion of said body, each said waistband portion defining first and second end portions, said first end portion of said first waistband portion being releasably secured to said first end portion of said second waistband portion, and said second end portion of said first waistband portion being releasably secured to said second end portion of said second waistband portion.

9. The pelvic area support of claim 5 wherein said support member defines front and rear portions on either side of said crotch portion, and wherein said harness includes a first end portion for being secured to said front portion and a second end portion for being secured to said rear portion.

10. The pelvic area support of claim 9 wherein said harness includes a front strap defining said first end portion of said harness and a rear strap defining said second end portion of said harness, and further including a pair of shoulder straps, each having a first end secured to said front strap and a second end secured to said rear strap.

11. The pelvic area support of claim 10 wherein said first and second end portions of said harness each carry a plurality of radiating tabs and wherein said pelvic area support is provided with means for releasably securing said tabs to said support member.

12. The pelvic area support of claim 11 wherein said means for releasably securing said tabs comprises a plurality of hook and loop fasteners.

13. The pelvic area support of claim 5 wherein said harness releasably engages said support member.

* * * * *